(12) United States Patent
Jalbert et al.

(10) Patent No.: US 9,316,622 B2
(45) Date of Patent: Apr. 19, 2016

(54) MICROWAVE VIBRATION SENSORS

(71) Applicant: Hamilton Sundstrand Corporation, Charlotte, NC (US)

(72) Inventors: Peter L. Jalbert, Granby, CT (US); Gary M. McBrien, S. Glastonbury, CT (US)

(73) Assignee: Hamilton Sundstrand Corporation, Charlotte, NC (US)

(*) Notice: Subject to any disclaimer, the term of this patent is extended or adjusted under 35 U.S.C. 154(b) by 295 days.

(21) Appl. No.: 13/889,763

(22) Filed: May 8, 2013

(65) Prior Publication Data
US 2014/0331773 A1 Nov. 13, 2014

(51) Int. Cl.
G01N 29/36 (2006.01)
G01H 9/00 (2006.01)
G10K 11/00 (2006.01)

(52) U.S. Cl.
CPC .............. *G01N 29/36* (2013.01); *G01H 9/00* (2013.01); *G10K 11/002* (2013.01)

(58) Field of Classification Search
CPC .............. G01N 23/20008; G01N 2035/00405; G01N 29/36; G01H 9/00; G10K 11/002
USPC .......................... 73/866.5, 1.86, 649; 248/550
See application file for complete search history.

(56) References Cited

U.S. PATENT DOCUMENTS

| | | | | |
|---|---|---|---|---|
| 4,403,336 A * | 9/1983 | Taniguchi et al. | | 378/35 |
| 4,481,825 A * | 11/1984 | Kljuev | | G01H 9/00 342/52 |
| 4,788,553 A * | 11/1988 | Phillips | | H01Q 19/08 343/753 |
| 5,479,826 A * | 1/1996 | Twerdochlib | | G01H 9/00 324/642 |
| 6,223,602 B1 * | 5/2001 | Kyrtsos | | G01H 1/003 73/597 |
| 7,825,669 B2 * | 11/2010 | Parsons | | G01S 13/36 324/637 |
| 8,593,156 B2 * | 11/2013 | Lee | | G01H 3/00 324/637 |
| 2010/0126288 A1 * | 5/2010 | Osswald | | 73/866.5 |
| 2012/0126794 A1 * | 5/2012 | Jensen | | G01D 5/48 324/149 |

OTHER PUBLICATIONS

Extended European Search Report Application No./Patent No. 14167538.9-1559/2801801 dated Nov. 6, 2015.

* cited by examiner

*Primary Examiner* — Laura Martin
*Assistant Examiner* — Suman K Nath
(74) *Attorney, Agent, or Firm* — Locke Lord LLP; Scott D. Wofsy; Joshua L. Jones

(57) ABSTRACT

A vibration sensor includes a probe body with a vibration isolator operatively connected to the probe body for isolation of the probe body from vibrations of a structure to be monitored for vibration. A waveguide is operatively connected to the probe body to convey microwaves to and from a surface for sensing vibration of the structure to be monitored for vibration.

4 Claims, 2 Drawing Sheets

MICROWAVE VIBRATION SENSORS

BACKGROUND OF THE INVENTION

1. Field of the Invention

The present invention relates to sensors, and more particularly to sensors for detecting vibrations such as in gas turbine engines.

2. Description of Related Art

A variety of sensor devices are known for detecting and monitoring vibrations. Piezoelectric sensors have often been used for this purpose. However, certain applications may preclude the use of piezoelectric sensors due to harsh conditions. For example, use of piezoelectric sensors in a gas turbine engine can be limited if the operating conditions are severe enough to shorten the sensor life, diminish the sensor reliability, or otherwise reduce the performance of the sensors. Temperature in particular is an important factor in shortening sensor life. Most sensors either have very short life at high temperatures or cannot operate at all. Additionally, piezoelectric sensors typically have relatively good sensitivity at higher frequencies, but in certain applications there may be a need for sensors to detect lower frequency vibrations than piezoelectric sensors are capable of detecting.

Such conventional methods and systems have generally been considered satisfactory for their intended purpose. However, there is still a need in the art for methods and devices that allow for improved ruggedness and frequency range in vibration sensors. There also remains a need in the art for such methods and devices that are easy to make and use. The present invention provides a solution for these problems.

SUMMARY OF THE INVENTION

The subject invention is directed to a new and useful vibration sensor. The vibration sensor includes a probe body with a vibration isolator operatively connected to the probe body for isolation of the probe body from vibrations of a structure to be monitored for vibration. A waveguide is operatively connected to the probe body to convey microwaves to and from a surface for sensing vibration of the structure to be monitored for vibration.

The mass of the probe body and at least one of a spring coefficient and a damping coefficient of the vibration isolator can be tuned to isolate the probe body from vibrations of a predetermined vibration frequency in the structure to be monitored for vibration. In certain embodiments, a cap is operatively connected to the vibration isolator with a space bounded by the probe body and cap for passage of microwaves to and from the wave guide. The cap can be configured and adapted to be mounted to a surface for sensing vibration thereof. A coaxial cable can be connected to the waveguide for conveyance of microwave signals to and from the waveguide.

In accordance with certain embodiments, a reflector is operatively connected to the probe body spaced apart from the waveguide for reflecting microwaves into the waveguide. The reflector can be operatively connected to a cap, such as the cap described above, within a space bounded by the probe body and cap. A pedestal can connect between the reflector and the cap. The mass of the reflector and at least one of a spring coefficient and a damper coefficient of the pedestal can be tuned to amplify vibration of the reflector in response to vibrations of a predetermined frequency in the structure to be monitored for vibrations.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1:
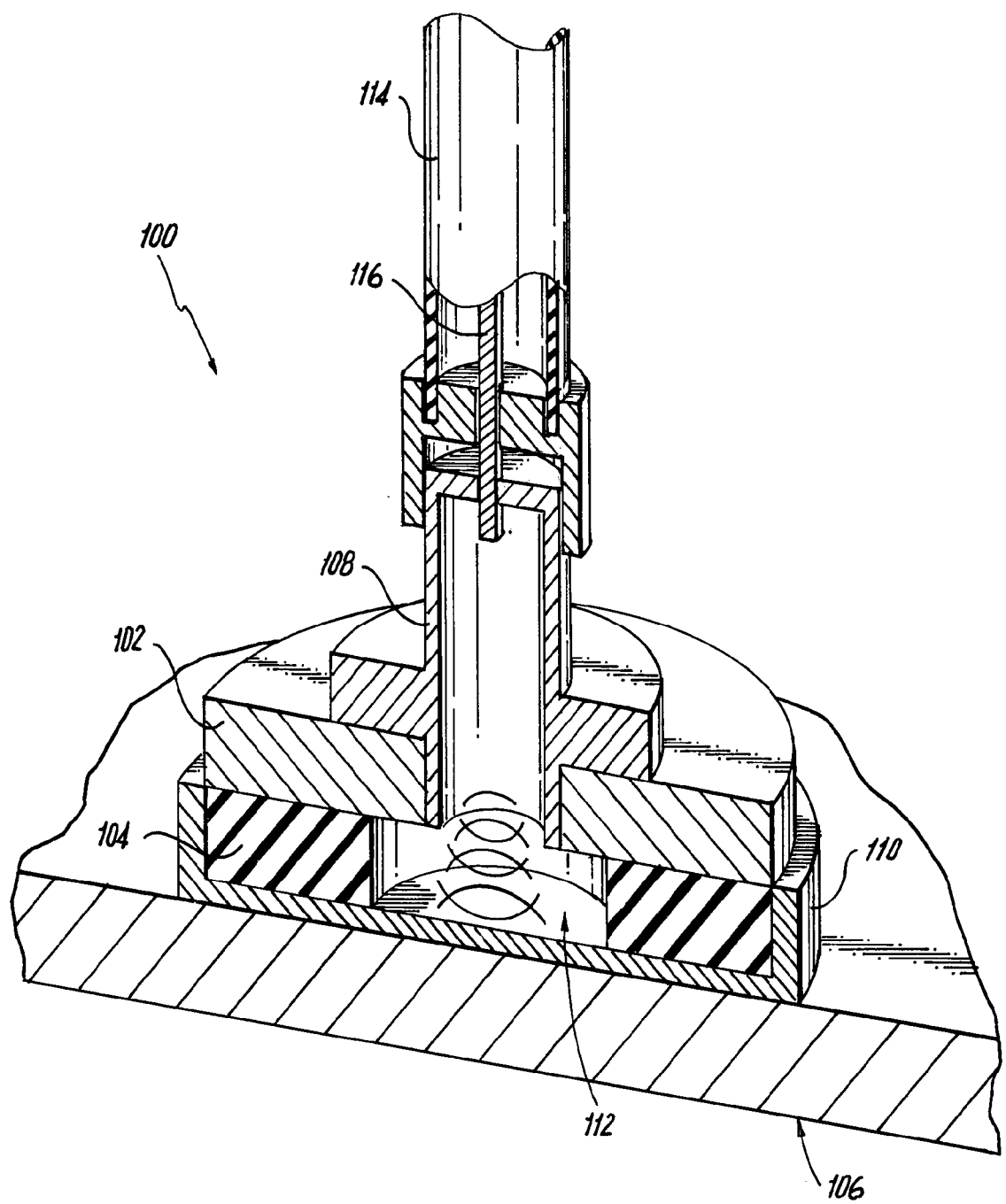
FIG. 1 is a cross-sectional perspective view of an exemplary embodiment of a vibration sensor constructed in accordance with the present invention, showing the probe body and associated vibration isolator.

Reference will now be made to the drawings wherein like reference numerals identify similar structural features or aspects of the subject invention. For purposes of explanation and illustration, and not limitation, a partial view of an exemplary embodiment of a vibration sensor in accordance with the invention is shown in FIG. 1 and is designated generally by reference character 100. Other embodiments of vibration sensors in accordance with the invention, or aspects thereof, are provided in FIG. 2, as will be described. The systems and methods of the invention can be used for vibration detection in harsh environments such as in gas turbine engines.

Vibration sensor 100 includes a probe body 102 with a vibration isolator 104 operatively connected to probe body 102 for isolation of probe body 102 from vibrations of a structure to be monitored for vibration. For example, sensor 100 is mounted to surface 106 to monitor vibrations in the underlying structure. A waveguide 108 is operatively connected to probe body 102 to convey microwaves, indicated schematically in FIG. 1, to and from the interior surface of cap 110 for sensing vibration. Cap 110 is connected to vibration isolator 104 with an interior space 112 bounded by probe body 102, vibration isolator 104, and cap 110 for passage of microwaves to and from wave guide 108. Cap 110 can be mounted to any suitable surface for sensing vibration thereof using an adhesive, fastener or the like, and serves to protect interior space 112 and vibration isolator 104. Those skilled in the art will readily appreciate that cap 110 is optional, and that vibration isolator 104 can be mounted directly to a surface to be monitored in suitable applications. For example, if the surface being monitored has adequate reflective properties, vibration isolator 104 can be mounted directly to the surface without a cap therebetween.

The mass of probe body 102 and the spring and damping coefficients of vibration isolator 104 can be tuned to isolate probe body 102 from vibrations of a predetermined vibration frequency or range of frequencies. Frequencies of interest may include, for example, the frequencies of blades passing structures, and fundamental and harmonic frequencies of rotating parts such as gears shafts, high and low turbine rotors, and the like. For example, the materials and dimensions of probe body 102 and vibration isolator 104 can be tailored to isolate probe body 102 from a desired vibration frequency for a given application. In certain applications sensor 100 is generally tuned to reject frequencies, e.g., probe body 102 will not move, above a certain predetermined limit, so that sensor 100 will read frequencies above that predetermined limit. When the underlying structure vibrates at or above the predetermined frequency, vibration isolator 104 will isolate probe body 102 from the vibration. The underlying structure will therefore vibrate relative to probe body 102 and this relative vibration will be detectable as described below.

Coaxial cable 114 is connected to waveguide 108 for conveyance of microwave signals to and from waveguide 108. Core 116 of coaxial cable 114 protrudes into waveguide 108 to serve as a microwave antenna. Waveguide 108 is otherwise hollow, and serves to deliver microwaves from coaxial cable 114 to cap 110, and to return reflected microwaves from cap 110 to coaxial cable 114. Cap 110 is mounted to surface 106 intimately so as to vibrate with surface 106. As the interior surface of cap 110 vibrates relative to probe body 102 and waveguide 108, the microwave signal returning to coaxial cable 114 can be interfered with the source signal to provide a modulated signal. As the modulated signal is monitored, vibration of surface 106 will manifest as changes in the modulated signal. Those skilled in the art will readily appreciate that interferometry is an exemplary way of producing a modulated signal, and that any other suitable method of monitoring microwaves can be used without departing from the scope of this disclosure. For example, another way to measure the vibration is simple phase variation over time of the incoming signal, relative to its average value.

Figure 2:
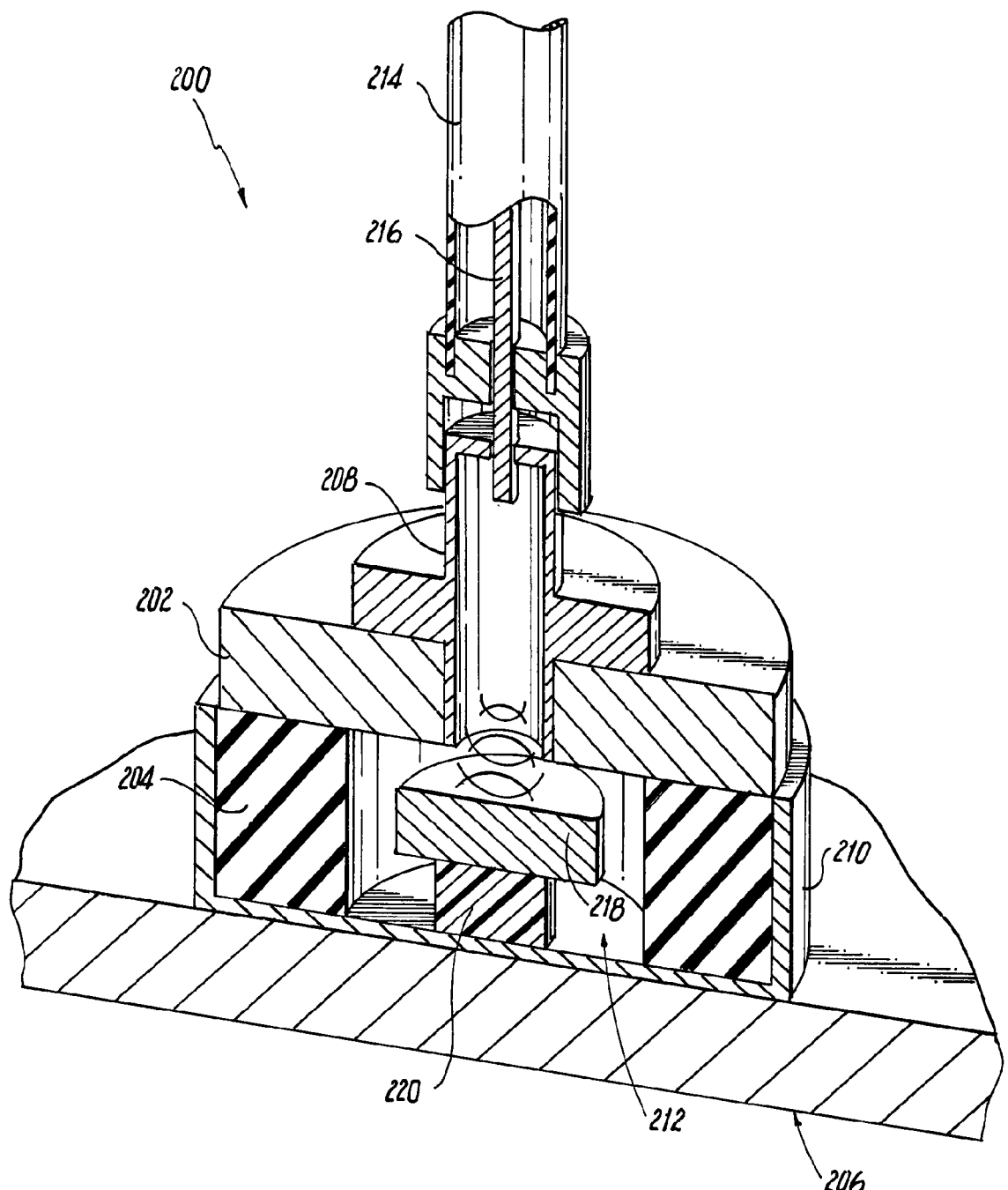
FIG. 2 is a cross-sectional perspective view of another exemplary embodiment of a vibration sensor constructed in accordance with the present invention, showing a reflector within the space bounded by the probe body and cap for amplifying vibration displacement for the sensor.

With reference now to FIG. 2, another exemplary embodiment of a vibration sensor 200 includes a mechanism for amplifying vibrations. Vibration sensor 200 includes a probe body 202, vibration isolator 204, waveguide 208, cap 210, interior space 212, coaxial cable 214, and core 216 and is mounted to a surface 206 much as described above with respect to FIG. 1. A reflector 218 is operatively connected to probe body 202 spaced apart from waveguide 208 for reflecting microwaves into waveguide 208, as indicated schematically in FIG. 2. Reflector 218 is connected to cap 210 by way of pedestal 220 and is situated within interior space 212. The mass of reflector 218 and the spring and damper coefficients of pedestal 220 can be tuned, e.g., by selection of suitable materials and/or dimensions, to amplify vibration displacement of the reflector in response to vibrations of a predetermined frequency in the structure underlying surface 206. This boosting of vibration displacement allows larger signals to be generated from microwave reflection from a target so tuned, than would be the case without such a target. For example, the spring mass damper system of reflector 218 can be tuned to amplify the same vibration frequency that the spring mass damper system of vibration isolator 204 is tuned to isolate from probe body 202. This tuning increases sensitivity of vibration sensor 200. Those skilled in the art will readily appreciate that the sensor components described above can be tuned to any suitable frequency as needed for particular applications without departing from the scope of this disclosure.

Potential advantages of the systems and methods described herein over traditional vibration sensors, such as piezoelectric sensors, include ruggedness to withstand harsh environments with better reliability. This can allow sensors as described herein to operate outside the temperature limits for traditional piezoelectric sensors, for example including high temperatures such as in gas turbine engines. Additionally, sensors as described herein can optionally be tuned to frequencies outside the practical limits of traditional piezoelectric sensors.

The methods and systems of the present invention, as described above and shown in the drawings, provide for vibration detection with superior properties. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A vibration sensor comprising:
   a probe body with a vibration isolator operatively connected to the probe body for isolation of the probe body from vibrations of a structure to be monitored for vibration;
   a waveguide operatively connected to the probe body to convey microwaves toward and away from a surface for sensing vibration of the structure to be monitored for vibration; and
   a microwave reflective cap operatively connected to the vibration isolator with a space bounded by the probe body and cap for passage of microwaves to and from the wave guide, wherein the cap is configured and adapted to be mounted to the surface for sensing vibration thereof.

2. A vibration sensor as recited in claim 1, further comprising a coaxial cable operatively connected to the waveguide for conveyance of microwave signals to and from the waveguide.

3. A vibration sensor as recited in claim 1, wherein the probe body has a mass, and wherein the mass of the probe body and at least one of a spring coefficient and a damping coefficient of the vibration isolator are tuned to isolate the probe body from vibrations of a predetermined vibration frequency in the structure to be monitored for vibration.

4. A vibration sensor comprising:
   a probe body with a vibration isolator operatively connected to the probe body for isolation of the probe body from vibrations of a structure to be monitored for vibration;
   a waveguide operatively connected to the probe body to convey microwaves to and from a surface for sensing vibration of the structure to be monitored for vibration;
   a reflector operatively connected to the probe body spaced apart from the waveguide for reflecting microwaves into the waveguide;
   a cap operatively connected to the vibration isolator, wherein the cap is configured and adapted to be mounted to a surface for sensing vibration thereof, and wherein the reflector is operatively connected to the cap within a space bounded by the probe body and cap; and
   a pedestal connecting between the reflector and the cap, wherein the reflector has a mass, and wherein the mass of the reflector and at least one of a spring coefficient and a damper coefficient of the pedestal are tuned to amplify vibration of the reflector in response to vibrations of a predetermined frequency in the structure to be monitored for vibrations.

\* \* \* \* \*